US006696556B2

(12) United States Patent
Snapir et al.

(10) Patent No.: US 6,696,556 B2
(45) Date of Patent: Feb. 24, 2004

(54) DNA MOLECULE ENCODING A VARIANT $\alpha_{2B}$-ADRENOCEPTOR PROTEIN, AND USES THEREOF

(75) Inventors: Amir Snapir, Turku (FI); Paula Heinonen, Turku (FI); Pia Alhopuro, Turku (FI); Matti Karvonen, Turku (FI); Markku Koulu, Turku (FI); Ullamari Pesonen, Turku (FI); Mika Scheinin, Naantali (FI); Jukka T. Salonen, Jännevirta (FI); Tomi-Pekka Tuomainen, Kuopio (FI); Timo A. Lakka, Kuopio (FI); Kristiina Nyyssönen, Kuopio (FI); Riitta Salonen, Jännevirta (FI); Jussi Kauhanen, Kuopio (FI); Veli-Pekka Valkonen, Kuopio (FI)

(73) Assignee: OY Juvantia Pharma Ltd. (FI)

( * ) Notice: Subject to any disclaimer, the term of this patent is extended or adjusted under 35 U.S.C. 154(b) by 0 days.

(21) Appl. No.: 09/825,923

(22) Filed: Apr. 5, 2001

(65) Prior Publication Data

US 2001/0016338 A1 Aug. 23, 2001

Related U.S. Application Data

(62) Division of application No. 09/422,985, filed on Oct. 22, 1999.

(51) Int. Cl.[7] .................. C12N 15/11; C07H 21/04; C07K 14/00

(52) U.S. Cl. .................. 536/23.1; 536/23.5; 536/24.31; 530/350

(58) Field of Search .............................. 435/69.1, 320.1, 435/325; 530/350; 536/23.5, 23.1, 24.31

(56) References Cited

U.S. PATENT DOCUMENTS

| 5,053,337 A | | 10/1991 | Weinshank et al. | |
|---|---|---|---|---|
| 5,350,836 A | * | 9/1994 | Kopchick et al. | ........... 530/399 |
| 5,595,880 A | | 1/1997 | Weinshank et al. | |
| 5,861,309 A | | 1/1999 | Bard et al. | |

OTHER PUBLICATIONS

Snapir, A., et al, 2001, J. Am. Coll. Cardiol., 37(6): 1516–1522.*
Ji, et al, 1998, J. Biol. Chem, 273: 17299–17302.*
Baldwin, C.T. et al., "Identification of a Polymorphic Glutamic Acid Stretch in the $\alpha_{2B}$–Adrenergic Receptor and Lack of Linkage with Essential Hypertension," *Am. J. Hyper.* 12:853–857 (1999).
Baumgart, D. et al., "Augmented $\alpha$–Adrenergic Constriction of Atherosclerotic Human Coronary Arteries," *Circulation* 99:2090–2097 (1999).

Heinonen, P. et al., "Identification of a three amino acid deletion in the alpha–2B–adrenergic receptor which is associated with reduced basal metabolic rate in obese subjects," *J. Clin. Endocrinol. Metab.* 84:2429–2433 (1999).
Jewell–Motz, E. et al., "An acidic motif within the third intracellular loop of the alpha2C2 adrenergic receptor is required for agonist–promoted phosphorylation and desensitization," *Biochem.* 34:11946–11953 (1995).
Julius, B.K. et al. (1999). "Alpha–adrenoceptor blockade prevents exercise–induce vasoconstriction of stenotic coronary arteries." *J. Am. Coll. Cardiology* 33:1499–1505.
Huchet, A.M., "Central $\alpha_1$–adrenoceptors and cardiovascular control in normotensive and spontaneously hypertensive rats," *Eur J Pharmacol,* 1983, 95:207–213.
Davey, M., "Mechanism of alpha blockade for blood pressure control," *Am J Cardiol,* 1987, 59:18G–28G.
Leech, C.J. and Faber, J.E., "Different $\alpha$–adrenoceptor subtypes mediate constriction of arterioles and venules," *Am J Physiol* 270 (*Heart and Circulatory Physiol* 39), 1996, :H710–H722.
Limberger, N. et al., "Pharmacological characterization of presynaptic $\alpha_2$–autoreceptors in rat submaxillary gland and heart atrium," *Br J Pharmacol,* 1992, 107:246–255.
Bockman, C.S. et al., "Binding and functional characterization of alpha–2 adrenergic receptor subtypes on pig vascular endothelium," *J Pharmacol Exp Therpeut,* 1993, 267:1126–1133.
Reid, J.L., "Alpha–adrenergic receptors and blood pressure control," *Am J Cardiol,* 1986, 57:6E–12E.
Ruffolo, Jr., R.R. et al., "Pharmacologic and Therapeutic applications of $\alpha_2$–adrenoceptor subtypes," *Annu Rev Pharmacol Toxicol,* 1993, 32:243–279.
Collins, P and Sheridan, D., "Improvement angina pectoris wiht alpha adrenoceptor blockade," *Br Heart J,* 1985, 53:488–492.
Bylund, D.B., "Subtypes of $\alpha_1$– and $\alpha_2$–adrenergic receptors," *FASEB J,* 1992, 6:832–839.

(List continued on next page.)

*Primary Examiner*—Elizabeth Kemmerer
*Assistant Examiner*—Sandra Wegert
(74) *Attorney, Agent, or Firm*—Rothwell, Figg, Ernst & Manbeck, p.c.

(57) ABSTRACT

This invention relates to a DNA sequence comprising a nucleotide sequence encoding a variant $\alpha_{2B}$-adrenoceptor protein and to the variant $\alpha_{2B}$-adrenoceptor protein as well as a method for screening a subject to determine if the subject is a carrier of a variant gene that encodes the variant $\alpha_{2B}$-adrenoceptor protein. Further this invention relates to a method for treating a mammal suffering from vascular contraction of coronary arteries, the method comprising the step of administering a selective $\alpha_{2B}$-adrenoceptor antagonist to the mammal and to transgenic animals comprising a human DNA molecule encoding human $\alpha_{2B}$-adrenoceptor protein or the variant $\alpha_{2B}$-adrenoceptor protein.

6 Claims, No Drawings

OTHER PUBLICATIONS

Snapir, A. et al., "An insertion/deletion polymorphism in the $\alpha_{2B}$–adrenergic receptor gene is a novel genetic risk factor for acute coronary events," *J Am Coll Card,* 2001, 37:1516–1522.

Phillips, J.K. et al., "Receptors involved in nerve–mediated vasocontriction in small arteries of the rat hepatic mesentery," *Br J Pharmacol,* 1998, 124:1403–1412.

Michel, A.D. et al., "Assessment of imiloxan as a selective $\alpha_{2B}$–adrenoceptor antagonist," *Br J Pharmacol,* 1990, 99:560–564.

Link, R.E. et al., "Cardiovascular regulation in mice lacking $\alpha_2$–adrenergic receptor subtypes b and c," *Science,* 1996, 273:803–805.

MacMillan, L.B. et al., "Central hypotensive effects of the $\alpha_{2a}$–adrenergic receptor subtype," *Science,* 1996, 273:801–803.

Richman, J.G. and Regan, J.W., "$\alpha_2$–Adrenergic receptors increase cell migration and decrease F–actin labeling in rat aortic smooth muscle cells," *Am J Physiol,* 1998, 274 (*Cell Physiol* 43):C654–C662.

Wilber, D.J. et al., "$\alpha$–Adrenergic infulences in canine ischemic sudden death: effects of $\alpha_1$–adrenoceptor blockade with prazosin," *J Cardiovasc Pharmacol,* 1987, 10:96–106.

Indolfi, C. et al., "Role of $\alpha_2$–adrenoceptoes in normal and atherosclerotic human coronary circulation," *Circulation,* 1992, 86:1116–1124.

Handy, D.E. et al., "Diverse tissue expression of rat $\alpha_2$–adrenergic receptor genes," *Hypertension,* 1993, 21:861–865.

Hodgson, J.M. et al., Effects of regional $\alpha$– and $\beta$–blockade on resting and hyperemic coronary blood flow in conscious, unstressed humans, *Circulation,* 1989, 79:797–809.

Redfern, W.S. et al., "The role of $\alpha_2$–adrenoreceptors in the vasculature of the rat tail," *Br J Pharmacol,* 1995, 114:1724–1730.

Tavares, A. et al., "Localization of $\alpha_{2A}$– and $\alpha_{2B}$–adrenergic receptor subtypes in brain," *Hypertension,* 1996, 27:449–455.

* cited by examiner

DNA MOLECULE ENCODING A VARIANT $\alpha_{2B}$-ADRENOCEPTOR PROTEIN, AND USES THEREOF This application is a divisional of application Ser. No. 09/422,985 filed Oct. 22, 1999, which is incorporated herein by reference.

FIELD OF THE INVENTION

This invention relates to a DNA molecule encoding a variant human $\alpha_{2B}$-adrenoceptor, said variant $\alpha_{2B}$-adrenoceptor protein and a method to assess the risk of individuals to suffer from vascular contraction of coronary arteries in mammals as well as a method for the treatment of vascular contraction of coronary arteries. This invention also relates to transgenic animals comprising a human DNA molecule encoding human $\alpha_{2B}$-adrenoceptor or said variant $\alpha_{2B}$-adrenoceptor.

BACKGROUND OF THE INVENTION

The publications and other materials used herein to illuminate the background of the invention, and in particular, cases to provide additional details respecting the practice, are incorporated by reference.

The $\alpha_2$-adrenoceptors $\alpha_2$-ARs) mediate many of the physiological effects of the catecholamines norepinephrine and epinephrine. Three genetic subtypes of $\alpha_2$-adrenoceptors are known in humans and other mammals, denoted as $\alpha_{2A}$-, $\alpha_{2B}$-, and $\alpha_{2C}$-adrenoceptors. The human genes encoding the receptors are located on chromosomes 10, 2 and 4, respectively. No splice variants are known to exist of these receptors, as the genes are intronless. The tissue distributions and physiological and pharmacological functions of the receptor subtypes have been reviewed e.g. by MacDonald et al. (1997) and Docherty (1998). Based on recent studies with gene-targeted and transgenic mice, $\alpha_{2A}$-adrenoceptors mediate most of the pharmacological actions ascribed to currently available $\alpha_2$-adrenoceptor agonists, including inhibition of neurotransmitter release, central hypotensive and bradycardic effects, sedation and anesthesia, and analgesia. The same studies indicate that $\alpha_{2B}$-adrenoceptors mediate peripheral vasoconstriction in response to agonist activation (Link et al. 1996, Macmillan et al. 1996). Other physiological or pharmacological effects have not been associated with certainty with this receptor subtype. The $\alpha_{2C}$-adrenoceptor subtype appears to be involved in regulation of complex behaviors. It is not known that this subtype would have important functions in peripheral tissues outside the central nervous system or in cardiovascular regulation.

Coronary heart disease (CHD), like many other common disorders, arises from complex interactions between genetic and environmental factors. It is reasonable to assume that functionally important genetic variation in mechanisms important for the regulation of vascular functions, including the coronary vasculature, will be found to be associated with the pathogenesis and therapy of CHD. A variant form of the human $\alpha_{2B}$-AR gene was recently identified (Heinonen et al., 1999). The variant allele encodes a receptor protein with a deletion of three glutamate residues in an acidic stretch of 18 amino acids (of which 15 are glutamates) located in the third intracellular loop of the receptor polypeptide. This acidic stretch is a unique feature in the primary structure of $\alpha_{2B}$-AR in comparison to $\alpha_{2A}$-AR and $\alpha_{2C}$-AR, suggesting that the motif has a distinct role in the function of $\alpha_{2B}$-AR. Amino acid sequence alignment of $\alpha_{2B}$-AR polypeptides of different mammals reveals that the acidic stretch is highly conserved among the $\alpha_{2B}$-ARs of mammals and that the acidic stretch is long in humans in comparison to other species. This suggests that the motif is important for the functionality of the receptor, and that the short form (D for "deletion") probably represents the ancestral form and the long form (I for "insertion") could well represent a more recent allelic variant in humans. Jewell-Motz and Liggett (1995) studied the in vitro functions of this stretch using site-directed mutagenesis to delete as well as to substitute 16 amino acids of the stretch. Their results suggest that this acidic motif is necessary for full agonist-promoted receptor phosphorylation and desensitization.

Based on the vasoconstrictive property of $\alpha_{2B}$-AR in mice and the involvement of this acidic region in the desensitization mechanism of the receptor, we hypothesized that the deletion variant confers reduced receptor desensitization and therefore augmented vasoconstriction that could be associated with cardiovascular pathologies. To test this hypothesis, we carried out a 4-year prospective study in 912 middle-aged Finnish men.

OBJECT AND SUMMARY OF THE INVENTION

One object of this invention is to provide a DNA sequence of a variant human $\alpha_{2B}$-adrenoceptor gene and the corresponding variant $\alpha_{2B}$-adrenoceptor protein.

Another object of the invention is to provide a method for screening a subject to assess if an individual is at risk to suffer from vascular contraction of coronary arteries.

A third object of the invention is to provide a method for the treatment of vascular contraction of coronary arteries of mammals.

A fourth object of the invention is to provide a transgenic animal with a gene encoding a human $\alpha_{2B}$-adrenoceptor or said variant thereof.

Thus, according to one aspect the invention concerns a DNA sequence comprising a nucleotide sequence encoding a variant $\alpha_{2B}$-adrenoceptor protein with a deletion of at least 1 glutamate from a glutamic acid repeat element of 12 glutamates, amino acids 298–309, in an acidic stretch of 18 amino acids 294–311, located in the $3^{rd}$ intracellular loop of the receptor polypeptide.

The invention further concerns a variant $\alpha_{2B}$-adrenoceptor protein with a deletion of at least 1 glutamate from a glutamic acid repeat element of 12 glutamates, amino acids 298–309, in an acidic stretch of 18 amino acids 294–311, located in the $3^{rd}$ intracellular loop of the receptor polypeptide.

According to another aspect the invention concerns a method for screening a subject to determine if said subject is a carrier of a said variant gene with both alleles encoding a said variant $\alpha_{2B}$-adrenoceptor, i.e. to determine if said subject's genotype of the human $\alpha_{2B}$-adrenoceptor is of the deletion/deletion (D/D) type, comprising the steps of a) providing a biological sample of the subject to be screened, b) providing an assay for detecting in the biological sample the presence of
  i) the insertion/insertion (I/I) or deletion/insertion (D/I) genotypes of the human $\alpha_{2B}$-adrenoceptor, or
  ii) the D/D genotype of the human $\alpha_{2B}$-adrenoceptor, and c) assessing at least one of the two following
  i) an individual's risk to develop a disease involving vascular contraction of coronary arteries, or
  ii) an individual's need for $\alpha_{2B}$-selective or $\alpha_{2B}$-nonselective $\alpha_2$-adrenoceptor antagonist therapy, based on whether said subject is of said D/D genotype or not.

According to a third aspect the present invention concerns a method for treating a mammal suffering from vascular contraction of coronary arteries, said method comprising the step of administering a selective $\alpha_{2B}$-adrenoceptor antagonist to said mammal.

According to a fourth aspect the present invention concerns a transgenic animal which carries a human DNA sequence comprising a nucleotide sequence encoding a human $\alpha_{2B}$-adrenoceptor protein or a variant thereof.

DETAILED DESCRIPTION OF THE INVENTION

The present invention relates to a DNA molecule encoding a variant human $\alpha_{2B}$-adrenoceptor, said variant $\alpha_{2B}$-adrenoceptor protein and a method to assess the risk of individuals to suffer from vascular contraction of coronary arteries in mammals as well as a method for the treatment of vascular contraction of coronary arteries. The present invention also relates to transgenic animals comprising a human DNA molecule encoding a human $\alpha_{2B}$-adrenoceptor or said variant $\alpha_{2B}$-adrenoceptor protein.

The word treating shall also be understood to include preventing.

The concept "a deletion of at least 1 glutamate from a glutamic acid repeat element of 12 glutamates" refers to any deletion of 1 to 12 glutamates irrespective of the specific location in, or how many glutamates from said repeat element of 12 glutamates, amino acids 298–309 (SEQ ID NO: 4), in an acidic stretch of 18 amino acids 294–311 located in the $3^{rd}$ intracellular loop of the receptor polypeptide are deleted.

The concept "deletion/deletion (D/D) genotype of the human $\alpha_{2B}$-adrenoceptor", in short "D/D genotype", refers to a genotype of an individual having both $\alpha_{2B}$-adrenoceptor alleles code for a variant $\alpha_{2B}$-adrenoceptor with a deletion of at least 1 glutamate from a glutamic acid repeat element of 12 glutamates, amino acids 298–309, in an acidic stretch of 18 amino acids 294–311 (SEQ ID NO: 4), located in the $3^{rd}$ intracellular loop of the receptor polypeptide. Correspondingly "deletion/insertion (D/I) genotype" refers to a genotype having one of the gene alleles code for an $\alpha_{2B}$-adrenoceptor with a said deletion and the other without a said deletion, i.e. with a respective insertion, and thus the "insertion/insertion (I/I) genotype" refers to a genotype having both alleles code for an $\alpha_{2B}$-adrenoceptor without said deletion or deletions.

We recently identified a common variant form (SEQ ID NO: 1) of the human $\alpha_{2B}$-AR gene (SEQ ID NO: 3). This variant gene encodes a receptor protein (SEQ ID NO: 2) with a deletion of 3 glutamates, amino acids 307–309, from a glutamic acid (Glu) repeat element of 12 glutamates, amino acids 298–309, in an acidic stretch of 18 amino acids 294–311 (SEQ ID NO: 4), located in the $3^{rd}$ intracellular loop of the receptor polypeptide. This variant gene (SEQ ID NO: 1) was associated with decreased basal metabolic rate (BMR) in a group of obese Finnish subjects (Heinonen et al. 1999). Of the 166 obese subjects, 47 (28%) were homozygous for the long 12 glutamate repeat element ($Glu^{12}/Glu^{12}$), whereas 90 (54%) were heterozygous ($Glu^{12}/Glu^9$) and 29 (17%) were homozygous for the short form ($Glu^9/Glu^9$).

The results to be presented below show that in a population-based cohort of 912 Finnish middle-aged men subjects homozygous for the short form ($Glu^9/Glu^9$) described above, thus representing a deletion/deletion (D/D) genotype of the $\alpha_{2B}$-adrenoceptor, have a significantly elevated risk for acute coronary events in a four-year follow-up study. The risk for an acute coronary event, defined as definite or possible acute myocardial infarction (AMI) or prolonged (>20 min) chest pain requiring hospitalization, was increased 2.5 fold in subjects who had this D/D genotype. This increase in the risk for acute coronary events is as great as so far observed for any other genetic risk factor for acute coronary events or acute myocardial infarction in a prospective population study. Also the frequency of a study subject having a history of coronary heart disease (CHD) as well as CHD in an exercise test was associated with this D/D genotype. Based on these results and previous publications referred to above it can be postulated that this D/D genotype is related to an impaired capacity to downregulate $\alpha_{2B}$-adrenoceptor function during sustained receptor activation. Since altered $\alpha_{2B}$-adrenoceptor function seems to be of relevance in the pathogenesis of a significant fraction of all cases of acute coronary events in subjects with this D/D genotype (homozygous $Glu^9/Glu^9$) we believe it could also be of relevance in subjects with the insertion/deletion (I/D) (heterozygous $Glu^{12}/Glu^9$) and insertion/insertion (I/I) (homozygous $Glu^{12}/Glu^{12}$) genotypes when other risk factors for AMI are present. Further, since this specific deletion of 3 glutamates, amino acids 307–309, from said glutamic acid repeat element of 12 glutamates, amino acids 298–309, in said acidic stretch of 18 amino acids 294–311, located in the $3^{rd}$ intracellular loop of the receptor polypeptide seems to be of relevance in cases of AMI we believe that also other deletions, i.e. deletions of at least 1 glutamate, from said glutamic acid repeat element of 12 glutamates, amino acids 298–309, could be of relevance in the pathogenesis of AMI, because the $3^{rd}$ intracellular loop of the receptor polypeptide it is located in seems to have an essential role in the downregulation of the $\alpha_{2B}$-adrenoceptor.

Thus based on the results to be presented below and the publications referred to above an $\alpha_{2B}$-adrenoceptor antagonist would be useful for treating a mammal suffering from vascular contraction of coronary arteries.

Furthermore, an $\alpha_{2B}$-adrenoceptor antagonist selective for the $\alpha_{2B}$-adrenoceptor subtype would be therapeutically beneficial for the treatment of a disease involving said vascular contraction of coronary arteries. Such a disease could be clinically expressed as chronic angina pectoris, specifically e.g. AMI, unstable angina pectoris or Prinzmetal's variant form of angina pectoris. If $\alpha_{2B}$-adrenoceptor dependent vasoconstriction is a causative factor in some cases of AMI, then antagonism of these receptors should restore coronary circulation and reduce the ischemic myocardial damage. An $\alpha_{2B}$-adrenoceptor antagonist will relieve the vaso-constrictive component in the sustained ischemic episode of unstable angina pectoris, thus alleviating the symptoms and preventing AMI. Vasoconstriction is a key factor in the pathogenesis of Prinzmetal's angina, and an $\alpha_{2B}$-adrenoceptor antagonist may resolve and prevent attacks. An $\alpha_{2B}$-adrenoceptor antagonist will help to alleviate the vasoconstrictive component in all types of CHD, providing both symptomatic relief and protection from AMI.

$\alpha_{2B}$-adrenoceptors mediate vascular contraction of coronary arteries, and genetic polymorphism present in the $\alpha_{2B}$-adrenoceptor gene renders some subjects more susceptible to $\alpha_{2B}$-adrenoceptor mediated vasoconstriction of coronary arteries and associated clinical disorders. These subjects will especially benefit from treatment with an $\alpha_{2B}$-adrenoceptor antagonist, and will be at increased risk for adverse effects if subtype-nonselective $\alpha_2$-agonists are administered to them. Therefore, a gene test recognizing subjects with a deletion variant of the $\alpha_{2B}$-adrenoceptor gene will be useful in diagnostics and patient selection for specific therapeutic procedures. A gene test recognizing the D/D genotype of the $\alpha_{2B}$-adrenoceptor is useful in assessing an individual's risk to develop AMI and other clinical disorders involving vascular contraction of coronary arteries related to the D/D genotype. A gene test recognizing the D/D genotype of the $\alpha_{2B}$-adrenoceptor is useful in selecting drug therapy for patients with diseases involving vascular contraction of coronary arteries associated with the D/D genotype; subjects with the D/D genotype will especially benefit from therapy with $\alpha_2$-adrenoceptor antagonists $\alpha_{2B}$-selective or nonselective). A gene test recognizing the D/D genotype of the $\alpha_{2B}$-adrenoceptor is useful in selecting drug therapy for patients who might be at increased risk for adverse effects of $\alpha_2$-adrenergic agonists; either, it will be possible to avoid the use of $\alpha_2$-agonists in such patients, or it will be possible to include a specific $\alpha_{2B}$-antagonist in their therapeutic regimen.

The DNA sequence can be used for screening a subject to determine if said subject is a carrier of a variant gene. The determination can be carried out either as a DNA analysis according to well known methods, which include direct DNA sequencing of the normal and variant gene, allele specific amplification using the polymerase chain reaction (PCR) enabling detection of either normal or variant sequence, or by indirect detection of the normal or variant gene by various molecular biology methods including e.g. PCR-single stranded conformation polymorphism (SSCP) method or denaturing gradient gel electrophoresis (DGGE). Determination of the normal or variant gene can also be done by using a restriction fragment length polymorphism (RFLP) method, which is particularly suitable for genotyping large numbers of samples. Similarly, a test based on gene chip technology can be easily developed in analogy with many currently existing such tests for single-nucleotide polymorphisms.

The determination can also be carried out at the level of RNA by analyzing RNA expressed at tissue level using various methods. Allele specific probes can be designed for hybridization. Hybridization can be done e.g. using Northern blot, RNase protection assay or in situ hybridization methods. RNA derived from the normal or variant gene can also be analyzed by converting tissue RNA first to cDNA and thereafter amplifying cDNA by an allele specific PCR method.

As examples of useful $\alpha_{2B}$-adrenoceptor antagonists can be mentioned imiloxan[2-(1-ethyl-2-imidazoyl)methyl-1,4-benzodioxan, ARC-239 [2-[2-(4-(2-methoxy-phenyl)piperazin-1-yl)ethyl]-4,4-dimethyl-1,3-(2H,4H)-isoquinolindione], prazosin[1-(4-amino-6,7-dimethoxy-2-quinazolinyl)-4-(2-furanylcarbonyl)piperazine] and chlorpromazine[2-chloro-N,N-dimethyl-10H-phenothiazine-10-propanamine].

The required dosage of the compounds will vary with the particular condition being treated, the severity of the condition, the duration of the treatment, the administration route and the specific compound being employed. A typical therapeutically effective daily dose administered, e.g. orally or by infusion, can vary from e.g. 0.1 µg to 10 mg per kilogram body weight of an adult person.

Influence of the variant gene sequence can be investigated in transgenic animals. A transgenic animal can be generated e.g. using targeted homologous recombination methodology. This will provide an ideal preclinical model to investigate and screen new drug molecules, which are designed to modify the influence of the variant gene.

The invention will be described in more detail in the experimental section.

EXPERIMENTAL SECTION

Determination of Genomic Alleles Encoding the $\alpha_{2B}$-adrenoceptor

PCR-SSCA Analysis

The polymerase chain reaction-single stranded conformational analysis (PCR-SSCA) used to identify the genomic alleles encoding the $\alpha_{2B}$-adrenoceptor was carried out as follows: The genomic DNA encoding the $\alpha_{2B}$-adrenergic receptor was amplified in two parts specific for the intronless $\alpha_{2B}$-adrenoceptor gene sequence (Lomasney et al. 1990). The PCR primer pairs for PCR amplification were as follows: Pair 1: 5'-GGGGCGACGCTCTTGTCTA-3' (SEQ ID NO: 5) and 5'-GGTCTCCCCCTCCTCCTTC-3' (SEQ ID NO: 6) (product size 878 bp), pair 2: 5'-GCAGCAACCGCAGAGGTC-3' (SEQ ID NO: 7) and 5'-GGGCAAGAAGCAGGGTGAC-3' (SEQ ID NO: 8) (product size 814 bp). The primers were delivered by KeboLab (Helsinki, Finland). PCR amplification was conducted in a 5 µl volume containing 100 ng genomic DNA (isolated from whole blood), 2.5 mmol/l of each primer, 1.0 mmol/l deoxy-NTPs, 30 nmol/l $^{33}$P-dCTP and 0.25 U AmpliTaq DNA polymerase (Perkin Elmer Cetus, Norwalk, Conn.). PCR conditions were optimized using the PCR Optimizer™ kit (Invitrogen, San Diego, Calif.). Samples were amplified with a GeneAmp PCR System 9600 (Perkin Elmer Cetus). PCR products were digested with restriction enzymes for SSCA analysis. The product of primer pair 1 was digested with Dde I and Dra III (Promega Corp., Madison, Wis.). The product of primer pair 2 was digested with Alu I and Hinc II (Promega Corp.). The digested samples were mixed with SSCA buffer containing 95% formamide, 10 mmol/l NaOH, 0.05% xylene cyanol and 0.05% bromophenol blue (total volume 25 µl). Before loading, the samples were denatured for 5 min at 95° C. and kept 5 min on ice. Three microliters of each sample were loaded on MDE™ high-resolution gel (FMC, BioProducts, Rockland, Mass.). The gel electrophoresis was performed twice, at two different running conditions: 6% MDE gel at +4° C. and 3% MDE gel at room temperature, both at 4 W constant power for 16 h. The gels were dried and autoradiography was performed by apposing to Kodak BioMax MR film for 24 h at room temperature.

Sequencing and Genotyping

DNA samples migrating at different rates in SSCA were sequenced with the Thermo Sequenase™ Cycle Sequencing Kit (Amersham Life Science, Cleveland, Ohio).

For genotyping the identified 3-glutamic acid deletion, DNA was extracted from peripheral blood using standard methods. The $\alpha_{2B}$-AR I/D genotype was determined by separating PCR-amplified DNA fragments with electrophoresis. Based on the nature of the I/D variant, identification of the long and short alleles was achieved by their different electrophoretic migration rates due to their 9 bp size difference.

The region of interest was amplified using a sense primer 5'-AGGGTGTTTGTGGGGCATCT-3' (SEQ ID NO: 9) and an anti-sense primer 5'-CAAGCTGAGGCCGGA GACACT-3' (SEQ ID NO: 10) (Oligold, Eurogentec, Belgium), yielding a product size of 112 bp for the long allele (I) and 103 bp for the short allele (D). PCR amplification was conducted in a 10 µL volume containing ~100 ng genomic DNA, 1×buffer G (Invitrogen, San Diego, Calif., USA), 0.8 mM dNTPs, 0.3 µM of each primer and 0.25 units of AmpliTaq DNA polymerase (Perkin Elmer Cetus, Norwalk, Conn., USA). Samples were amplified with a GeneAmp PCR System 9600 (Perkin Elmer Cetus). After initial denaturation at 94° C. for 2 minutes, the samples were amplified over 35 cycles. PCR amplification conditions were 96° C. (40 s), 69° C. (30 s) and 72° C. (30 s) followed by final extension at 72° C. for 6 minutes. The PCR products representing the long and short alleles were identified by two alternative methods.

1) The amplified samples were mixed with 4 μl of stop solution (Thermo Sequenase™ Cycle Sequencing kit), heated to 95° C. for 2 min, and loaded hot onto sequencing gels (Long Ranger™, FMC). The gels were dried and autoradiography was performed as previously described.

2) Separation of the amplified PCR products was performed with electrophoresis on a high-resolution 4% Metaphor agarose gel (FMC Bioproducts, Rockland, Me.) and the bands were visualized by ethidium bromide staining. In both methods, the long ($Glu^{12}$) and short ($Glu^9$) alleles were identified based on their different electrophoretic migration rates.

Follow-up Study

The above referred four-year follow-up study of 912 Finnish middle-aged men subjects including 192 subjects with a specific deletion/deletion (D/D) genotype of the $\alpha_{2B}$-adrenoceptor is described in more detail in the following:

Knowing the vasoconstrictive property of $\alpha_{2B}$-AR in mice and the possible involvement of the investigated acidic region in the desensitization mechanism of the receptor we hypothesized that the observed insertion/deletion allelic variation could be associated with cardiovascular pathologies such as AMI. To test this hypothesis, we carried out a four-year follow-up study in 912 middle-aged Finnish men with no prior history of AMI. The study was carried out as part of the Kuopio Ischemic Heart Disease Risk Factor Study (KIHD), which is an ongoing population-based study designed to investigate risk factors for cardiovascular diseases and related outcomes in men from eastern Finland (Salonen 1988). This area is known for its homogenous population (Sajantila et al. 1996) and high coronary morbidity and mortality rates (Keys 1980).

Of the 912 subjects, 192 (21%) had the D/D genotype, 256 (28%) had the I/I genotype and 464 (51%) were heterozygous i.e. I/D. This genotype distribution is in Hardy-Weinberg equilibrium (p=0.46).

Of the 37 cases that had an acute coronary event during the follow-up, 18 were classified as definite AMI, 12 as possible AMI and seven as prolonged chest pain. Among the subjects with the D/D genotype, 15 (8%) had an acute coronary event during the follow-up time. The corresponding incidences for the I/I and the heterozygous genotypes i.e. I/D were 10 (4%) and 12 (3%). The observed cumulative incidence of acute coronary events differed significantly among the different genotypes (p=0.008). No significant difference in the cumulative incidence of acute coronary events was found between the I/D and the I/I genotypes (p=0.4) (table 1). There was a significant difference (log-rank p=0.0045) between the D/D subgroup and the other two genotypes combined in the cumulative event-free time in the Kaplan-Meier survival function, demonstrating that there is a consistently increased incidence of acute coronary events in the D/D subgroup.

The D/D genotype was associated with a 2.5 fold increased risk for an acute coronary event (95% CI=1.3–4.8, p=0.006) in comparison to the other two genotypes combined. The relative risk remained above 2 after adjustment for major CHD risk factors (table 2).

The D/D subgroup was not significantly different from the I/D+I/I subgroup in terms of many known major risk factors for CHD. From 87 variables in the study database only 5 were significantly different between the D/D and the I/D+I/I genotype subgroups: 1. there were more acute coronary events in the D/D subgroup (8% vs. 3%, p=0.006), 2. history of CHD was more prevalent in the D/D subgroup (37% vs. 29%, p=0.043), 3. the prevalence of CHD in exercise test was higher in the D/D subgroup (30% vs. 22%, p=0.036), 4. mean hemoglobin level was higher in the D/D subgroup (149.0 g/l vs. 146.8 g/l, p=0.005) and 5. mean dietary cholesterol intake (4-days) was lower in the D/D subgroup (411.6 mg vs. 440.1 mg, p=0.033) (table 3). The first four observed differences support our hypothesis that the D/D genotype confers reduced receptor desensitization and therefore augmented vasoconstriction. This augmented vasoconstriction is the reason for the increased incidence of acute coronary events, the higher prevalence of CHD in exercise and history of CHD. We hypothesize that the increased level of hemoglobin is due to relative anoxia of tissues because of this augmented vasoconstriction.

To examine the possibility that the D/D genotype is a genetic marker for acute coronary events rather than a causative factor, we have searched the literature for known genetic risk factors for acute coronary events and AMI and their chromosomal localization. All but one (Apo-B) are on different chromosomes than the $\alpha_{2B}$-AR gene (chromosome 2) and the gene for Apo-B is neither in the physical nor the genetic vicinity of the $\alpha_{2B}$-AR gene. Cox regression analysis revealed that the increased RR for acute coronary events in the D/D subgroup is not affected by the serum Apo-B concentration.

Taken together, the known biological properties of the $\alpha_{2B}$-AR, the homogeneity of the Finnish population with its relatively high incidence of CHD, the study design, the relatively large representative study population and the clustering of the findings around one trait suggest that the D/D receptor allele is a causal genetic risk factor for acute coronary events.

TABLE 1

The cumulative incidence of acute coronary events among men with different genotypes of the $\alpha_{2B}$-AR (p values are stated below)

| Genotype | | Events (% of men at risk) | Men at risk (% of all) |
| --- | --- | --- | --- |
| D/D | observed | 15 (8) | 192 (21) |
| | expected | 7.8 | |
| I/D | observed | 12 (3) | 464 (51) |
| | expected | 18.8 | |
| I/I | observed | 10 (4) | 256 (28) |
| | expected | 10.4 | |
| I/D + I/I | observed | 22 (3) | 720 (79) |
| | expected | 29.2 | |
| Total | observed | 37 (4) | 912 (100) |

P values for the above table:
D/D vs. I/D vs. I/I    p = 0.008
D/D vs. I/D            p = 0.002
D/D vs. I/I            p = 0.038
I/D vs. I/I            p = 0.389
D/D vs. I/D + I/I      p = 0.005

TABLE 2

Relative risk (RR) and its 95% confidence interval (CI) for an acute coronary event - a comparison of each of the genotypes with the other two combined. Results of a Cox regression model for 37 acute coronary events in a population sample of 912 subjects

| Genotype | Events/men at risk | RR (95% CI) p | Adjusted RR (95% CI) p |
|---|---|---|---|
| D/D | 15/192 | 2.5(1.3–4.8) 0.006 | 2.3(1.2–4.5) 0.014 |
| I/D | 12/464 | 0.44(0.2–0.9) 0.020 | 0.5(0.2–1.0) 0.052 |
| I/I | 10/256 | 1.03(0.5–2.1) 0.940 | 0.96(0.5–2.0) 0.901 |

Adjustment was done for age, CHD in the family, high cholesterol in the family, hypertension and smoking

TABLE 3

List of all significant differences ($p < 0.05$) between the D/D and the I/D + I/I genotype subgroups among 87 variables in the study database

| Variable | D/D | I/D + I/I | p |
|---|---|---|---|
| Acute coronary events [event/n (%)] | 15/192 (8) | 22/720 (3) | 0.006 |
| Ischemic findings in exercise test [case/n (%)] | 57/192 (30) | 160/720 (22) | 0.036 |
| History of CHD [case/n (%)] | 71/192 (37) | 209/720 (29) | 0.043 |
| Mean blood haemoglobin [g/L] | 149.0 | 146.8 | 0.005 |
| Mean 4 day dietary cholesterol intake [mg] | 411.6 | 440.1 | 0.033 |

% = Percent of men at risk

It will be appreciated that the methods of the present invention can be incorporated in the form of a variety of embodiments, only a few of which are disclosed herein. It will be apparent for the specialist in the field that other embodiments exist and do not depart from the spirit of the invention. Thus, the described embodiments are illustrative and should not be construed as restrictive.

References

Docherty J R: Subtypes of functional $\alpha_1$- and $\alpha_2$-receptors. *Eur J Pharmacol* 1998;361:1–15

Heinonen P, Koulu M, Pesonen U, Karvonen M, Rissanen A, Laakso M, Valve R, Uusitupa M, Scheinin M: Identification of a three amino acid deletion in the alpha-2B-adrenergic receptor which is associated with reduced basal metabolic rate in obese subjects. *J Clin Endocrinol Metab* 1999;84:2429–2433

Jewell-Motz E, Liggett S B: An acidic motif within the third intracellular loop of the alpha2C2 adrenergic receptor is required for agonist-promoted phosphorylation and desensitization. *Biochemistry* 1995;34:11946–11953

Keys A: *Seven Countries: A Multivariate Analysis of Death and Coronary Heart Disease.* Cambridge, Mass., Harvard University Press, 1980

Link R E, Desai K, Hein L, Stevens M E, Chruscinski A, Bernstein D, Barsh G S, Kobilka B K: Cardiovascular regulation in mice lacking alpha2-adrenergic receptor subtypes b and c. *Science* 1996;273:803–805

Lomasney J W, Lorenz W, Allen L F, King K, Regan J W, Yang-Feng T L, Caron M C, Lefkowitz R J: Expansion of the alpha-2 adrenergic receptor family: cloning and characterization of a human alpha-2 adrenergic receptor subtype, the gene for which is located on chromosome 2. *Proc Natl Acad Sci USA.* 1990;87:5094–5098.

MacDonald E, Kobilka B K, Scheinin M: Gene targeting—homing in on $\alpha_2$-adrenoceptor subtype function. *Trends Pharmacol Sci* 1997;18:211–219

MacMillan L B, Hein L, Smith M S, Piascik M T, Limbird L E: Central hypotensive effects of the alpha2a-adrenergic receptor subtype. *Science* 1996;273:801–803

Sajantila A, Salem A H, Savolainen P, Bauer K, Gierig C, Paabo S: Paternal and maternal DNA lineages reveal a bottleneck in the founding of the Finnish population. *Proc.Natl.Acad.Sci. U.S.A.* 1996;93:12035–12039

Salonen J T: Is there a continuing need for longitudinal epidemiologic research? The Kuopio Ischaemic Heart Disease Risk Factor Study. *Ann.Clin Res* 1988;20:46–50

What is claimed is:

1. An isolated DNA sequence comprising a nucleotide sequence encoding a variant $\alpha_{2B}$-adrenoceptor protein wherein the variation is a deletion of 3 glutamate residues from a glutamic acid repeat element of 12 glutamate residues, amino acids 298–309, in a wildtype $\alpha_{2B}$-adrenoceptor protein having an amino acid sequence set forth in SEQ ID NO:4.

2. The isolated DNA sequence according to claim 1 comprising the genomic nucleotide sequence of SEQ ID NO:1.

3. The isolated DNA sequence according to claim 1 comprising the amino acid sequence of SEQ ID NO:2.

4. The isolated DNA sequence of according to claim 1 wherein said DNA sequence is cDNA.

5. An isolated RNA sequence comprising an RNA sequence corresponding to the isolated DNA sequence of claim 1.

6. A hybridizing probe which comprises a single strand of the cDNA according to claim 4.

* * * * *

SEQUENCE LISTING

```
<160> NUMBER OF SEQ ID NOS: 10

<210> SEQ ID NO 1
<211> LENGTH: 1344
<212> TYPE: DNA
<213> ORGANISM: Homo sapiens
<220> FEATURE:
<221> NAME/KEY: CDS
<222> LOCATION: (1)..(1341)
<223> OTHER INFORMATION: Coding sequence for variant human
      alpha-2B-adrenoceptor protein

<400> SEQUENCE: 1 atg gac cac cag gac ccc tac tcc gtg cag gcc aca gcg gcc ata gcg      48
Met Asp His Gln Asp Pro Tyr Ser Val Gln Ala Thr Ala Ala Ile Ala
  1               5                  10                  15 gcg gcc atc acc ttc ctc att ctc ttt acc atc ttc ggc aac gct ctg      96
Ala Ala Ile Thr Phe Leu Ile Leu Phe Thr Ile Phe Gly Asn Ala Leu
             20                  25                  30 gtc atc ctg gct gtg ttg acc agc cgc tcg ctg cgc gcc cct cag aac     144
Val Ile Leu Ala Val Leu Thr Ser Arg Ser Leu Arg Ala Pro Gln Asn
         35                  40                  45
```

-continued

```
ctg ttc ctg gtg tcg ctg gcc gcc gcc gac atc ctg gtg gcc acg ctc       192
Leu Phe Leu Val Ser Leu Ala Ala Ala Asp Ile Leu Val Ala Thr Leu
    50                  55                  60 atc atc cct ttc tcg ctg gcc aac gag ctg ctg ggc tac tgg tac ttc       240
Ile Ile Pro Phe Ser Leu Ala Asn Glu Leu Leu Gly Tyr Trp Tyr Phe
65                  70                  75                  80 cgg cgc acg tgg tgc gag gtg tac ctg gcg ctc gac gtg ctc ttc tgc       288
Arg Arg Thr Trp Cys Glu Val Tyr Leu Ala Leu Asp Val Leu Phe Cys
                85                  90                  95 acc tcg tcc atc gtg cac ctg tgc gcc atc agc ctg gac cgc tac tgg       336
Thr Ser Ser Ile Val His Leu Cys Ala Ile Ser Leu Asp Arg Tyr Trp
            100                 105                 110 gcc gtg agc cgc gcg ctg gag tac aac tcc aag cgc acc ccg cgc cgc       384
Ala Val Ser Arg Ala Leu Glu Tyr Asn Ser Lys Arg Thr Pro Arg Arg
        115                 120                 125 atc aag tgc atc atc ctc act gtg tgg ctc atc gcc gcc gtc atc tcg       432
Ile Lys Cys Ile Ile Leu Thr Val Trp Leu Ile Ala Ala Val Ile Ser
    130                 135                 140 ctg ccg ccc ctc atc tac aag ggc gac cag ggc ccc cag ccg cgc ggg       480
Leu Pro Pro Leu Ile Tyr Lys Gly Asp Gln Gly Pro Gln Pro Arg Gly
145                 150                 155                 160 cgc ccc cag tgc aag ctc aac cag gag gcc tgg tac atc ctg gcc tcc       528
Arg Pro Gln Cys Lys Leu Asn Gln Glu Ala Trp Tyr Ile Leu Ala Ser
                165                 170                 175 agc atc gga tct ttc ttt gct cct tgc ctc atc atg atc ctt gtc tac       576
Ser Ile Gly Ser Phe Phe Ala Pro Cys Leu Ile Met Ile Leu Val Tyr
            180                 185                 190 ctg cgc atc tac ctg atc gcc aaa cgc agc aac cgc aga ggt ccc agg       624
Leu Arg Ile Tyr Leu Ile Ala Lys Arg Ser Asn Arg Arg Gly Pro Arg
        195                 200                 205 gcc aag ggg ggg cct ggg cag ggt gag tcc aag cag ccc cga ccc gac       672
Ala Lys Gly Gly Pro Gly Gln Gly Glu Ser Lys Gln Pro Arg Pro Asp
    210                 215                 220 cat ggt ggg gct ttg gcc tca gcc aaa ctg cca gcc ctg gcc tct gtg       720
His Gly Gly Ala Leu Ala Ser Ala Lys Leu Pro Ala Leu Ala Ser Val
225                 230                 235                 240 gct tct gcc aga gag gtc aac gga cac tcg aag tcc act ggg gag aag       768
Ala Ser Ala Arg Glu Val Asn Gly His Ser Lys Ser Thr Gly Glu Lys
                245                 250                 255 gag gag ggg gag acc cct gaa gat act ggg acc cgg gcc ttg cca ccc       816
Glu Glu Gly Glu Thr Pro Glu Asp Thr Gly Thr Arg Ala Leu Pro Pro
            260                 265                 270 agt tgg gct gcc ctt ccc aac tca ggc cag ggc cag aag gag ggt gtt       864
Ser Trp Ala Ala Leu Pro Asn Ser Gly Gln Gly Gln Lys Glu Gly Val
        275                 280                 285 tgt ggg gca tct cca gag gat gaa gct gaa gag gag gaa gag gag           912
Cys Gly Ala Ser Pro Glu Asp Glu Ala Glu Glu Glu Glu Glu Glu
    290                 295                 300 gag gag tgt gaa ccc cag gca gtg cca gtg tct ccg gcc tca gct tgc       960
Glu Glu Cys Glu Pro Gln Ala Val Pro Val Ser Pro Ala Ser Ala Cys
305                 310                 315                 320 agc ccc ccg ctg cag cag cca cag ggc tcc cgg gtg ctg gcc acc cta      1008
Ser Pro Pro Leu Gln Gln Pro Gln Gly Ser Arg Val Leu Ala Thr Leu
                325                 330                 335 cgt ggc cag gtg ctc ctg ggc agg ggc gtg ggt gct ata ggt ggg cag      1056
Arg Gly Gln Val Leu Leu Gly Arg Gly Val Gly Ala Ile Gly Gly Gln
            340                 345                 350 tgg tgg cgt cga cgg gcg cag ctg acc cgg gag aag cgc ttc acc ttc      1104
Trp Trp Arg Arg Arg Ala Gln Leu Thr Arg Glu Lys Arg Phe Thr Phe
```

```
                        355                 360                 365
gtg ctg gct gtg gtc att ggc gtt ttt gtg ctc tgc tgg ttc ccc ttc    1152
Val Leu Ala Val Val Ile Gly Val Phe Val Leu Cys Trp Phe Pro Phe
    370                 375                 380 ttc ttc agc tac agc ctg ggc gcc atc tgc ccg aag cac tgc aag gtg    1200
Phe Phe Ser Tyr Ser Leu Gly Ala Ile Cys Pro Lys His Cys Lys Val
385                 390                 395                 400 ccc cat ggc ctc ttc cag ttc ttc tgg atc ggc tac tgc aac agc        1248
Pro His Gly Leu Phe Gln Phe Phe Trp Ile Gly Tyr Cys Asn Ser
                405                 410                 415 tca ctg aac cct gtt atc tac acc atc ttc aac cag gac ttc cgc cgt    1296
Ser Leu Asn Pro Val Ile Tyr Thr Ile Phe Asn Gln Asp Phe Arg Arg
                420                 425                 430 gcc ttc cgg agg atc ctg tgc cgc ccg tgg acc cag acg gcc tgg tga    1344
Ala Phe Arg Arg Ile Leu Cys Arg Pro Trp Thr Gln Thr Ala Trp
            435                 440                 445

<210> SEQ ID NO 2
<211> LENGTH: 447
<212> TYPE: PRT
<213> ORGANISM: Homo sapiens

<400> SEQUENCE: 2

Met Asp His Gln Asp Pro Tyr Ser Val Gln Ala Thr Ala Ala Ile Ala
 1               5                  10                  15

Ala Ala Ile Thr Phe Leu Ile Leu Phe Thr Ile Phe Gly Asn Ala Leu
            20                  25                  30

Val Ile Leu Ala Val Leu Thr Ser Arg Ser Leu Arg Ala Pro Gln Asn
        35                  40                  45

Leu Phe Leu Val Ser Leu Ala Ala Asp Ile Leu Val Ala Thr Leu
    50                  55                  60

Ile Ile Pro Phe Ser Leu Ala Asn Glu Leu Leu Gly Tyr Trp Tyr Phe
65                  70                  75                  80

Arg Arg Thr Trp Cys Glu Val Tyr Leu Ala Leu Asp Val Leu Phe Cys
                85                  90                  95

Thr Ser Ser Ile Val His Leu Cys Ala Ile Ser Leu Asp Arg Tyr Trp
            100                 105                 110

Ala Val Ser Arg Ala Leu Glu Tyr Asn Ser Lys Arg Thr Pro Arg Arg
        115                 120                 125

Ile Lys Cys Ile Ile Leu Thr Val Trp Leu Ile Ala Ala Val Ile Ser
    130                 135                 140

Leu Pro Pro Leu Ile Tyr Lys Gly Asp Gln Gly Pro Gln Pro Arg Gly
145                 150                 155                 160

Arg Pro Gln Cys Lys Leu Asn Gln Glu Ala Trp Tyr Ile Leu Ala Ser
                165                 170                 175

Ser Ile Gly Ser Phe Phe Ala Pro Cys Leu Ile Met Ile Leu Val Tyr
            180                 185                 190

Leu Arg Ile Tyr Leu Ile Ala Lys Arg Ser Asn Arg Arg Gly Pro Arg
        195                 200                 205

Ala Lys Gly Gly Pro Gly Gln Gly Glu Ser Lys Gln Pro Arg Pro Asp
    210                 215                 220

His Gly Gly Ala Leu Ala Ser Ala Lys Leu Pro Ala Leu Ala Ser Val
225                 230                 235                 240

Ala Ser Ala Arg Glu Val Asn Gly His Ser Lys Ser Thr Gly Glu Lys
                245                 250                 255

Glu Glu Gly Glu Thr Pro Glu Asp Thr Gly Thr Arg Ala Leu Pro Pro
```

-continued

```
                 260                 265                 270
Ser Trp Ala Ala Leu Pro Asn Ser Gly Gln Gly Gln Lys Glu Gly Val
            275                 280                 285

Cys Gly Ala Ser Pro Glu Asp Glu Ala Glu Glu Glu Glu Glu Glu Glu
        290                 295                 300

Glu Glu Cys Glu Pro Gln Ala Val Pro Val Ser Pro Ala Ser Ala Cys
305                 310                 315                 320

Ser Pro Pro Leu Gln Gln Pro Gln Gly Ser Arg Val Leu Ala Thr Leu
            325                 330                 335

Arg Gly Gln Val Leu Leu Gly Arg Gly Val Gly Ala Ile Gly Gly Gln
        340                 345                 350

Trp Trp Arg Arg Arg Ala Gln Leu Thr Arg Glu Lys Arg Phe Thr Phe
            355                 360                 365

Val Leu Ala Val Val Ile Gly Val Phe Val Leu Cys Trp Phe Pro Phe
        370                 375                 380

Phe Phe Ser Tyr Ser Leu Gly Ala Ile Cys Pro Lys His Cys Lys Val
385                 390                 395                 400

Pro His Gly Leu Phe Gln Phe Phe Phe Trp Ile Gly Tyr Cys Asn Ser
            405                 410                 415

Ser Leu Asn Pro Val Ile Tyr Thr Ile Phe Asn Gln Asp Phe Arg Arg
        420                 425                 430

Ala Phe Arg Arg Ile Leu Cys Arg Pro Trp Thr Gln Thr Ala Trp
            435                 440                 445

<210> SEQ ID NO 3
<211> LENGTH: 1353
<212> TYPE: DNA
<213> ORGANISM: Homo sapiens
<220> FEATURE:
<221> NAME/KEY: CDS
<222> LOCATION: (1)..(1350)
<223> OTHER INFORMATION: Coding sequence for human alpha-2B-adrenoceptor
      protein

<400> SEQUENCE: 3 atg gac cac cag gac ccc tac tcc gtg cag gcc aca gcg gcc ata gcg        48
Met Asp His Gln Asp Pro Tyr Ser Val Gln Ala Thr Ala Ala Ile Ala
 1               5                  10                  15 gcg gcc atc acc ttc ctc att ctc ttt acc atc ttc ggc aac gct ctg        96
Ala Ala Ile Thr Phe Leu Ile Leu Phe Thr Ile Phe Gly Asn Ala Leu
            20                  25                  30 gtc atc ctg gct gtg ttg acc agc cgc tcg ctg cgc gcc cct cag aac       144
Val Ile Leu Ala Val Leu Thr Ser Arg Ser Leu Arg Ala Pro Gln Asn
        35                  40                  45 ctg ttc ctg gtg tcg ctg gcc gcc gcc gac atc ctg gtg gcc acg ctc       192
Leu Phe Leu Val Ser Leu Ala Ala Ala Asp Ile Leu Val Ala Thr Leu
    50                  55                  60 atc atc cct ttc tcg ctg gcc aac gag ctg ctg ggc tac tgg tac ttc       240
Ile Ile Pro Phe Ser Leu Ala Asn Glu Leu Leu Gly Tyr Trp Tyr Phe
65                  70                  75                  80 cgg cgc acg tgg tgc gag gtg tac ctg gcg ctc gac gtg ctc ttc tgc       288
Arg Arg Thr Trp Cys Glu Val Tyr Leu Ala Leu Asp Val Leu Phe Cys
                85                  90                  95 acc tcg tcc atc gtg cac ctg tgc gcc atc agc ctg gac cgc tac tgg       336
Thr Ser Ser Ile Val His Leu Cys Ala Ile Ser Leu Asp Arg Tyr Trp
            100                 105                 110 gcc gtg agc cgc gcg ctg gag tac aac tcc aag cgc acc ccg cgc cgc       384
Ala Val Ser Arg Ala Leu Glu Tyr Asn Ser Lys Arg Thr Pro Arg Arg
        115                 120                 125
```

| | |
|---|---|
| atc aag tgc atc atc ctc act gtg tgg ctc atc gcc gcc gtc atc tcg<br>Ile Lys Cys Ile Ile Leu Thr Val Trp Leu Ile Ala Ala Val Ile Ser<br>130                135                140 | 432 |
| ctg ccg ccc ctc atc tac aag ggc gac cag ggc ccc cag ccg cgc ggg<br>Leu Pro Pro Leu Ile Tyr Lys Gly Asp Gln Gly Pro Gln Pro Arg Gly<br>145                  150              155              160 | 480 |
| cgc ccc cag tgc aag ctc aac cag gag gcc tgg tac atc ctg gcc tcc<br>Arg Pro Gln Cys Lys Leu Asn Gln Glu Ala Trp Tyr Ile Leu Ala Ser<br>                165              170              175 | 528 |
| agc atc gga tct ttc ttt gct cct tgc ctc atc atg atc ctt gtc tac<br>Ser Ile Gly Ser Phe Phe Ala Pro Cys Leu Ile Met Ile Leu Val Tyr<br>                  180              185              190 | 576 |
| ctg cgc atc tac ctg atc gcc aaa cgc agc aac cgc aga ggt ccc agg<br>Leu Arg Ile Tyr Leu Ile Ala Lys Arg Ser Asn Arg Arg Gly Pro Arg<br>        195              200              205 | 624 |
| gcc aag ggg ggg cct ggg cag ggt gag tcc aag cag ccc cga ccc gac<br>Ala Lys Gly Gly Pro Gly Gln Gly Glu Ser Lys Gln Pro Arg Pro Asp<br>210                215              220 | 672 |
| cat ggt ggg gct ttg gcc tca gcc aaa ctg cca gcc ctg gcc tct gtg<br>His Gly Gly Ala Leu Ala Ser Ala Lys Leu Pro Ala Leu Ala Ser Val<br>225                230              235              240 | 720 |
| gct tct gcc aga gag gtc aac gga cac tcg aag tcc act ggg gag aag<br>Ala Ser Ala Arg Glu Val Asn Gly His Ser Lys Ser Thr Gly Glu Lys<br>                245              250              255 | 768 |
| gag gag ggg gag acc cct gaa gat act ggg acc cgg gcc ttg cca ccc<br>Glu Glu Gly Glu Thr Pro Glu Asp Thr Gly Thr Arg Ala Leu Pro Pro<br>                  260              265              270 | 816 |
| agt tgg gct gcc ctt ccc aac tca ggc cag ggc cag aag gag ggt gtt<br>Ser Trp Ala Ala Leu Pro Asn Ser Gly Gln Gly Gln Lys Glu Gly Val<br>        275              280              285 | 864 |
| tgt ggg gca tct cca gag gat gaa gct gaa gag gag gaa gag gag gag<br>Cys Gly Ala Ser Pro Glu Asp Glu Ala Glu Glu Glu Glu Glu Glu Glu<br>290                295              300 | 912 |
| gag gag gag gaa gag tgt gaa ccc cag gca gtg cca gtg tct ccg gcc<br>Glu Glu Glu Glu Glu Cys Glu Pro Gln Ala Val Pro Val Ser Pro Ala<br>305                310              315              320 | 960 |
| tca gct tgc agc ccc ccg ctg cag cag cca cag ggc tcc cgg gtg ctg<br>Ser Ala Cys Ser Pro Pro Leu Gln Gln Pro Gln Gly Ser Arg Val Leu<br>                325              330              335 | 1008 |
| gcc acc cta cgt ggc cag gtg ctc ctg ggc agg ggc gtg ggt gct ata<br>Ala Thr Leu Arg Gly Gln Val Leu Leu Gly Arg Gly Val Gly Ala Ile<br>                340              345              350 | 1056 |
| ggt ggg cag tgg tgg cgt cga cgg gcg cag ctg acc cgg gag aag cgc<br>Gly Gly Gln Trp Trp Arg Arg Arg Ala Gln Leu Thr Arg Glu Lys Arg<br>        355              360              365 | 1104 |
| ttc acc ttc gtg ctg gct gtg gtc att ggc gtt ttt gtg ctc tgc tgg<br>Phe Thr Phe Val Leu Ala Val Val Ile Gly Val Phe Val Leu Cys Trp<br>370                375              380 | 1152 |
| ttc ccc ttc ttc ttc agc tac agc ctg ggc gcc atc tgc ccg aag cac<br>Phe Pro Phe Phe Phe Ser Tyr Ser Leu Gly Ala Ile Cys Pro Lys His<br>385                390              395              400 | 1200 |
| tgc aag gtg ccc cat ggc ctc ttc cag ttc ttc ttc tgg atc ggc tac<br>Cys Lys Val Pro His Gly Leu Phe Gln Phe Phe Phe Trp Ile Gly Tyr<br>                405              410              415 | 1248 |
| tgc aac agc tca ctg aac cct gtt atc tac acc atc ttc aac cag gac<br>Cys Asn Ser Ser Leu Asn Pro Val Ile Tyr Thr Ile Phe Asn Gln Asp<br>        420              425              430 | 1296 |
| ttc cgc cgt gcc ttc cgg agg atc ctg tgc cgc ccg tgg acc cag acg<br>Phe Arg Arg Ala Phe Arg Arg Ile Leu Cys Arg Pro Trp Thr Gln Thr | 1344 |

```
                435                 440                 445
gcc tgg tga                                                                    1353
Ala Trp
    450

<210> SEQ ID NO 4
<211> LENGTH: 450
<212> TYPE: PRT
<213> ORGANISM: Homo sapiens

<400> SEQUENCE: 4

Met Asp His Gln Asp Pro Tyr Ser Val Gln Ala Thr Ala Ala Ile Ala
 1               5                  10                  15

Ala Ala Ile Thr Phe Leu Ile Leu Phe Thr Ile Phe Gly Asn Ala Leu
            20                  25                  30

Val Ile Leu Ala Val Leu Thr Ser Arg Ser Leu Arg Ala Pro Gln Asn
        35                  40                  45

Leu Phe Leu Val Ser Leu Ala Ala Asp Ile Leu Val Ala Thr Leu
    50                  55                  60

Ile Ile Pro Phe Ser Leu Ala Asn Glu Leu Leu Gly Tyr Trp Tyr Phe
 65                  70                  75                  80

Arg Arg Thr Trp Cys Glu Val Tyr Leu Ala Leu Asp Val Leu Phe Cys
                85                  90                  95

Thr Ser Ser Ile Val His Leu Cys Ala Ile Ser Leu Asp Arg Tyr Trp
            100                 105                 110

Ala Val Ser Arg Ala Leu Glu Tyr Asn Ser Lys Arg Thr Pro Arg Arg
        115                 120                 125

Ile Lys Cys Ile Ile Leu Thr Val Trp Leu Ile Ala Ala Val Ile Ser
    130                 135                 140

Leu Pro Pro Leu Ile Tyr Lys Gly Asp Gln Gly Pro Gln Pro Arg Gly
145                 150                 155                 160

Arg Pro Gln Cys Lys Leu Asn Gln Glu Ala Trp Tyr Ile Leu Ala Ser
                165                 170                 175

Ser Ile Gly Ser Phe Phe Ala Pro Cys Leu Ile Met Ile Leu Val Tyr
            180                 185                 190

Leu Arg Ile Tyr Leu Ile Ala Lys Arg Ser Asn Arg Arg Gly Pro Arg
        195                 200                 205

Ala Lys Gly Gly Pro Gly Gln Gly Glu Ser Lys Gln Pro Arg Pro Asp
    210                 215                 220

His Gly Gly Ala Leu Ala Ser Ala Lys Leu Pro Ala Leu Ala Ser Val
225                 230                 235                 240

Ala Ser Ala Arg Glu Val Asn Gly His Ser Lys Ser Thr Gly Glu Lys
                245                 250                 255

Glu Glu Gly Glu Thr Pro Glu Asp Thr Gly Thr Arg Ala Leu Pro Pro
            260                 265                 270

Ser Trp Ala Ala Leu Pro Asn Ser Gly Gln Gly Gln Lys Glu Gly Val
        275                 280                 285

Cys Gly Ala Ser Pro Glu Asp Glu Ala Glu Glu Glu Glu Glu Glu Glu
    290                 295                 300

Glu Glu Glu Glu Glu Cys Glu Pro Gln Ala Val Pro Val Ser Pro Ala
305                 310                 315                 320

Ser Ala Cys Ser Pro Pro Leu Gln Gln Pro Gln Gly Ser Arg Val Leu
                325                 330                 335

Ala Thr Leu Arg Gly Gln Val Leu Leu Gly Arg Gly Val Gly Ala Ile
            340                 345                 350
```

Gly Gly Gln Trp Trp Arg Arg Arg Ala Gln Leu Thr Arg Glu Lys Arg
            355                 360                 365

Phe Thr Phe Val Leu Ala Val Val Ile Gly Val Phe Val Leu Cys Trp
        370                 375                 380

Phe Pro Phe Phe Phe Ser Tyr Ser Leu Gly Ala Ile Cys Pro Lys His
385                 390                 395                 400

Cys Lys Val Pro His Gly Leu Phe Gln Phe Phe Trp Ile Gly Tyr
                405                 410                 415

Cys Asn Ser Ser Leu Asn Pro Val Ile Tyr Thr Ile Phe Asn Gln Asp
            420                 425                 430

Phe Arg Arg Ala Phe Arg Arg Ile Leu Cys Arg Pro Trp Thr Gln Thr
        435                 440                 445

Ala Trp
    450

<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence: PCR primer
      pair

<400> SEQUENCE: 5
ggggcgacgc tcttgtcta                                                    19

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence: PCR primer
      pair

<400> SEQUENCE: 6
ggtctccccc tcctccttc                                                    19

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence: PCR primer
      pair

<400> SEQUENCE: 7
gcagcaaccg cagaggtc                                                     18

<210> SEQ ID NO 8
<211> LENGTH: 19
<212> TYPE: DNA
<213> ORGANISM: Artificial Sequence
<220> FEATURE:
<223> OTHER INFORMATION: Description of Artificial Sequence: PCR primer
      pair

<400> SEQUENCE: 8
gggcaagaag cagggtgac                                                    19

<210> SEQ ID NO 9
<211> LENGTH: 20
<212> TYPE: DNA
<213> ORGANISM: Artificial Sequence

```
<220> FEATURE:
<223> OTHER INFORMATION: Description of Artificial Sequence: PCR primer
      pair

<400> SEQUENCE: 9
agggtgtttg tggggcatct                                              20

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: PCR primer
      pair

<400> SEQUENCE: 10
caagctgagg ccggagacac t                                            21
```